US010200625B2

(12) United States Patent
Marcelpoil et al.

(10) Patent No.: US 10,200,625 B2
(45) Date of Patent: Feb. 5, 2019

(54) SYSTEM AND METHOD FOR IMAGE ACQUISITION USING SUPERVISED HIGH QUALITY IMAGING

(71) Applicant: BD Kiestra B.V., Drachten (NL)

(72) Inventors: Raphael R. Marcelpoil, Corenc (FR); Cedrick Orny, Grenoble (FR); Didier Morel, Grenoble (FR)

(73) Assignee: BD KIESTRA B.V., Drachten (NL)

( * ) Notice: Subject to any disclaimer, the term of this patent is extended or adjusted under 35 U.S.C. 154(b) by 157 days.

(21) Appl. No.: 15/115,715

(22) PCT Filed: Jan. 30, 2015

(86) PCT No.: PCT/EP2015/052017
§ 371 (c)(1),
(2) Date: Aug. 1, 2016

(87) PCT Pub. No.: WO2015/114121
PCT Pub. Date: Aug. 6, 2015

(65) Prior Publication Data
US 2017/0013181 A1    Jan. 12, 2017

Related U.S. Application Data

(60) Provisional application No. 61/933,426, filed on Jan. 30, 2014.

(51) Int. Cl.
G06K 9/00 (2006.01)
G01N 21/17 (2006.01)
(Continued)

(52) U.S. Cl.
CPC ......... *H04N 5/2352* (2013.01); *G01N 21/255* (2013.01); *G01N 21/274* (2013.01);
(Continued)

(58) Field of Classification Search
None
See application file for complete search history.

(56) References Cited

U.S. PATENT DOCUMENTS 4,700,298 A    10/1987  Palcic
4,724,215 A    2/1988   Farber et al.
(Continued)

FOREIGN PATENT DOCUMENTS

CN    102590087 A    7/2012
CN    203385649 U    1/2014
(Continued)

OTHER PUBLICATIONS

Ancin H., et al., "Advances in Automated 3-D Image Analysis of Cell Populations Imaged by Confocal Microscopy", Cytometry, 1996, pp. 221-234, vol. 25, No. 3.
(Continued)

*Primary Examiner* — Matthew Bella
*Assistant Examiner* — Jose M Torres
(74) *Attorney, Agent, or Firm* — Botos Churchill IP Law LLP

(57) ABSTRACT

An image capture system and method for imaging biological samples disposed in culture media supported by a plate. The system has a calibration module, an image acquisition module and an image presentation module. When the system receives a culture plate for imaging, default values for the culture plate and media are used to begin image acquisition at a given time. The captured image is then used to create a pixel by pixel map of the image. The system inspects the pixel-by-pixel map for saturated pixels and for signal to noise ratio and acquires a new image if the number of saturated pixels is at or above a predetermined threshold or the signal to noise ratio for the pixel is below a predetermined threshold. From this inspection a new value of photon (Continued)

flux and/or exposure time is determined and a new image is captured using the new value and the steps are repeated. Upon a determination that a predetermined threshold signal to noise ratio has been obtained for the non-saturated pixels, or when the predetermined upper threshold for the time interval for image acquisition is elapsed the system provides a final image for the given time.

14 Claims, 10 Drawing Sheets

(51) Int. Cl.
    *H04N 5/235*     (2006.01)
    *G01N 21/25*     (2006.01)
    *G01N 21/27*     (2006.01)
    *G01N 33/483*     (2006.01)
    *H04N 5/217*     (2011.01)

(52) U.S. Cl.
    CPC .......... *G01N 33/4833* (2013.01); *H04N 5/217* (2013.01); *H04N 5/2353* (2013.01); *G01N 2201/12* (2013.01)

(56) References Cited

U.S. PATENT DOCUMENTS

| | | | |
|---|---|---|---|
| 5,403,722 A | 4/1995 | Floeder et al. |
| 5,510,246 A | 4/1996 | Morgan |
| 5,694,478 A | 12/1997 | Braier et al. |
| 5,723,308 A | 3/1998 | Mach et al. |
| 5,976,892 A | 11/1999 | Bisconte |
| 6,122,396 A | 9/2000 | King et al. |
| 6,134,354 A | 10/2000 | Lee et al. |
| 6,345,115 B1 | 2/2002 | Ramm et al. |
| 6,385,272 B1 | 5/2002 | Takahashi |
| 6,453,060 B1 | 9/2002 | Riley et al. |
| 6,605,446 B2 | 8/2003 | Eden |
| 6,718,077 B1 | 4/2004 | Ferreira et al. |
| 7,060,955 B1 | 6/2006 | Wang |
| 7,065,236 B2 | 6/2006 | Marcelpoil et al. |
| 7,106,889 B1 | 9/2006 | Mahers et al. |
| 7,117,098 B1 | 10/2006 | Dunlay et al. |
| 7,298,886 B2 | 11/2007 | Plumb et al. |
| 7,319,031 B2 | 1/2008 | Vent et al. |
| 7,341,841 B2 | 3/2008 | Metzger et al. |
| 7,351,574 B2 | 4/2008 | Vent |
| 7,496,225 B2 | 2/2009 | Graessle et al. |
| 7,582,415 B2 | 9/2009 | Straus |
| 7,596,251 B2 | 9/2009 | Affleck et al. |
| 7,623,728 B2 | 11/2009 | Avinash et al. |
| 7,666,355 B2 | 2/2010 | Alavie |
| 7,732,743 B1* | 6/2010 | Buchin .................. G06T 5/50 250/208.1 |
| 7,738,689 B2 | 6/2010 | Plumb et al. |
| 7,796,815 B2 | 9/2010 | Muschler et al. |
| 7,863,552 B2 | 1/2011 | Cartlidge et al. |
| 7,865,008 B2 | 1/2011 | Graessle et al. |
| 7,884,869 B2 | 2/2011 | Shurboff et al. |
| 7,967,575 B2 | 6/2011 | Plumb et al. |
| 7,978,258 B2 | 7/2011 | Christiansen et al. |
| 7,989,209 B2 | 8/2011 | Marcelpoil et al. |
| 8,094,916 B2 | 1/2012 | Graessle et al. |
| 8,131,477 B2 | 3/2012 | Li et al. |
| 8,260,026 B2 | 9/2012 | Plumb et al. |
| 8,417,013 B2 | 4/2013 | Bolea et al. |
| 8,428,331 B2 | 4/2013 | DiMarzio et al. |
| 8,570,370 B2 | 10/2013 | McCollum et al. |
| 8,588,505 B2 | 11/2013 | Bolea |
| 8,759,080 B2 | 6/2014 | Graessle et al. |
| 8,831,326 B2 | 9/2014 | Nishida et al. |
| 8,840,840 B2 | 9/2014 | Bolea |
| 8,855,397 B2 | 10/2014 | Moy et al. |
| 8,895,255 B1 | 11/2014 | Goldberg et al. |
| 8,896,706 B2 | 11/2014 | van den Hengel et al. |
| 9,012,209 B2 | 4/2015 | Eden et al. |
| 9,042,967 B2 | 5/2015 | Dacosta et al. |
| 9,292,729 B2 | 3/2016 | Guthrie et al. |
| 9,359,631 B2 | 6/2016 | Dupoy et al. |
| 9,378,545 B2 | 6/2016 | Bise et al. |
| 9,400,242 B2 | 7/2016 | Allano et al. |
| 9,470,624 B2 | 10/2016 | Guthrie et al. |
| 9,567,621 B2 | 2/2017 | Robinson et al. |
| 9,576,181 B2 | 2/2017 | Allano et al. |
| 9,606,046 B2 | 3/2017 | Decaux et al. |
| 2002/0001402 A1 | 1/2002 | Berliner |
| 2002/0050988 A1 | 5/2002 | Petrov et al. |
| 2002/0196964 A1 | 12/2002 | Stone et al. |
| 2003/0091221 A1 | 5/2003 | Marcelpoil et al. |
| 2003/0138140 A1 | 7/2003 | Marcelpoil et al. |
| 2003/0227612 A1 | 12/2003 | Fein |
| 2004/0253660 A1 | 12/2004 | Gibbs et al. |
| 2005/0254722 A1 | 11/2005 | Fattal et al. |
| 2006/0173266 A1 | 8/2006 | Pawluczyk et al. |
| 2007/0177149 A1 | 8/2007 | Aronkyto |
| 2008/0297597 A1 | 12/2008 | Inomata et al. |
| 2010/0061618 A1 | 3/2010 | Marcelpoil et al. |
| 2010/0067775 A1 | 3/2010 | Marcelpoil et al. |
| 2010/0136549 A1* | 6/2010 | Christiansen .......... G06T 7/0012 435/6.1 |
| 2012/0013603 A1 | 1/2012 | Liu |
| 2012/0134603 A1 | 5/2012 | Pang et al. |
| 2012/0148142 A1 | 6/2012 | Ortyn et al. |
| 2014/0161330 A1* | 6/2014 | Allano ................. G01N 21/255 382/128 |
| 2014/0219553 A1 | 8/2014 | van den Hengel |
| 2014/0278136 A1 | 9/2014 | Shamsheyeva et al. |
| 2015/0225684 A1 | 8/2015 | Spicer et al. |
| 2015/0268163 A1 | 9/2015 | Dupoy et al. |
| 2015/0339513 A1 | 11/2015 | Bolea |
| 2015/0353983 A1 | 12/2015 | Drazek et al. |
| 2016/0060676 A1 | 3/2016 | Lei |
| 2016/0083686 A1 | 3/2016 | Triva |
| 2016/0093033 A1 | 3/2016 | Allano et al. |
| 2016/0098840 A1 | 4/2016 | Allano et al. |
| 2016/0328844 A1 | 11/2016 | Triva |

FOREIGN PATENT DOCUMENTS

| | | | |
|---|---|---|---|
| EP | 1065496 A2 | 1/2001 |
| EP | 2520923 A1 | 11/2012 |
| EP | 2578693 A1 | 4/2013 |
| EP | 1163362 B1 | 7/2013 |
| EP | 2430461 B1 | 3/2014 |
| EP | 2287284 B1 | 12/2016 |
| JP | H05-340816 A | 12/1993 |
| JP | 2005-504276 A | 2/2005 |
| JP | 2005-509140 A | 4/2005 |
| JP | 2012529065 A | 11/2012 |
| WO | 03025554 A2 | 3/2003 |
| WO | 2012/152769 A1 | 11/2012 |
| WO | 2012152768 A1 | 11/2012 |
| WO | 2014098994 A1 | 6/2014 |
| WO | 2015162364 A1 | 10/2015 |
| WO | 2015173490 A1 | 11/2015 |
| WO | 2016001555 A1 | 1/2016 |
| WO | 2016011534 A1 | 1/2016 |
| WO | 2016083744 A1 | 6/2016 |
| WO | 2016097092 A1 | 6/2016 |
| WO | 2016172388 A2 | 10/2016 |
| WO | 2017006055 A1 | 1/2017 |

OTHER PUBLICATIONS

Goesele, M., et al., "Color Calibrated High Dynamic Range Imaging with ICC Profiles", Proceedings of the 9th IS&T Color Imaging Conference, Scottsdale, Arizona, Nov. 6, 2001, pp. 286-290.
International Preliminary Examination Report on Patentability for International Application No. PCT /US2006/018516, dated Sep. 27, 2007 (pp. 1-14 ), including replacement claims (pp. 35-43).

(56) References Cited

OTHER PUBLICATIONS

Madden, B.C., "Extended Intensity Range Imaging", Tech. Report, Dec. 17, 1993, University of Pennsylvania, GRASP Laboratory, pp. 1-19.

Malpica, N. et al., "Automated Nuclear Segmentation in Fluorescence Microscopy", Science, Technology and Education of Microscopy: An Overview, Jan. 2005, pp. 614-621.

Malpica, N., et al., "Applying Watershed Algorithms to the Segmentation of Clustered Nuclei", Cytometry, Nov. 1, 1996, pp. 221-234, vol. 25, No. 3.

Office Action for Canadian Application No. 2,607,609; dated Oct. 23, 2012.

Office Action for Japanese Application No. 2008-511426 dated Oct. 2, 2012.

Office Action for Korean Application No. 10-2007-7028983 dated Jul. 24, 2012.

Office Action for Mexican Application No. MX/a/2007/0I40I6; dated Nov. 27, 2012.

Office Action for U.S. Appl. No. 12/620,670 dated Jan. 4, 2012.

Office Action for U.S. Appl. No. 12/620,670, dated Aug. 2, 2012.

Office Action for U.S. Appl. No. 12/620,701; dated Oct. 26, 2011.

Zhou, R., et al., "A Multiple Wavelength Algorithm in Color Image Analysis and its Applications in Stain Decomposition in Microscopy Images," Medical Physics, 1996, pp. 1997-I1986, vol. 23(12).

Allers, Elke et al., Single-Cell and Population Level Viral Infection Dynamics Revealed by PhageFISH, A Method to Visualize Intracellular and Free Viruses, , Environmental Microbiology, 2013, 15(8), pp. 2306-2318.

BD Kiestra Total Lab Automation, Proven Systems, Proven Results, BD Diagnostics, Oct. 2012.

Bennett, Eric, et al., Video Enhancement Using Per-Pixel Virtual Exposure, The Univ. of North Carolina at Chapel Hill.

CamerA PrimerA Manual Interactive (MI) User Manual, Kiestra Lab Automoation, Aug. 23, 2007.

International Search Report and Written Opinion for Application No. PCT/EP2015/052017 dated Jun. 15, 2015.

Lawless et al., Colonyzer: automated quantification of microorganism growth characteristics on solid agar, BMC Bioinformatics 2010, 11:287, http://biomedcentral.com/1471-2105/11/287.

Starizona's Guide to CCD Imaging, Oct. 30, 2013, pp. 1-8.

Chinese Search Report issued in corresponding CN Application No. 2015800064078, pp. 2.

* cited by examiner

SYSTEM AND METHOD FOR IMAGE ACQUISITION USING SUPERVISED HIGH QUALITY IMAGING

CROSS-REFERENCE TO RELATED APPLICATION

The present application is a national phase entry under 35 U.S.C. § 371 of International Application No. PCT/EP2015/052017 filed Jan. 30, 2015, published in English, which claims priority from U.S. Provisional Application No. 61/933,426 filed Jan. 30, 2014, all of which are incorporated herein by reference.

BACKGROUND OF THE INVENTION

High Dynamic Range (HDR) imaging is a digital imaging technique that captures a greater dynamic range between the lightest and darkest areas of an image. A process for automatically optimizing a dynamic range of pixel intensity obtained from a digital image is described in U.S. Pat. No. 7,978,258 to Christiansen et al. HDR takes several images at different exposure levels and uses an algorithm to stitch them together to create an image that has both dark and light spots, without compromising the quality of either one. However, HDR can present a distortion of reality because it distorts the intensity of the image overall. Accordingly, HDR techniques that enhance contrast without distorting the intensity of the image continue to be sought.

Techniques for enhancing an image of a biological sample are described in WO 2012/152769 to Allano et al. Among the problems with imaging such samples identified in Allano et al. are:

i) the size of the colonies being viewed;
ii) the proximity of one colony to another;
iii) the color mix of the colonies;
iv) the nature of the Petri Dish; and
v) the nature of the culture medium; as well as other factors.

Allano et al.'s proposed solution to the problem of imaging a biological sample is to prepare a source image created from images obtained at each color, removing predetermined absorption effects for the culture medium and the culture vessel and determining a value for photon flux and exposure time using a predetermined exposure to obtain an image which is then dissected into luminosity zones. From that, image luminosity is obtained and used to determine if the value for photon flux and exposure time used was correct or if a new value for photon flux and exposure time should be used for image capture.

Problems with the above techniques is that they do not provide a system with an ability to provide imaging conditions that can detect very subtle changes in contrast that are required for image-based detection/identification of microbes on growth media. Because image-based evidence of microbes and/or their growth on media is (or at least can be) difficult to detect, more robust techniques for imaging such samples are sought.

BRIEF SUMMARY OF THE INVENTION

Described herein is a system and method that enhances the image capture for images with low or variable contrast. One example of such a challenging imaging environment is that of bacterial colonies growing on agar growth plates. The bacterial colonies reflect the light differently from the agar. In addition, the bacterial colonies can vary from light colors to dark colors and reflect light differently than the agar. The time to capture an image of a colony is short (approximately one second). Typically, an image of the growth plate is taken every 3 to 6 hours.

An image is acquired in a series of N image acquisitions at each time interval "x" (i.e. $t_0, t_1 \ldots t_x$). The first acquisition (N=1) uses default values for the light intensity and exposure time, referred to herein as "photon flux and exposure time." The photon flux value defines the number of photons reaching the scene per unit time and unit area ((photon quantity)·(time$^{-1}$)·(area$^{-1}$)). The time being the integration time at the camera's sensor. The exposure time determines the number of photons captured by the sensor for one frame acquisition. Said another way, photon flux is rate of flow of photons from the light source and exposure time influences the quantity of those photons received by the sensor for image acquisition. For a given photon flux, exposure time controls image intensity.

One skilled in the art is aware of many different ways to control photon flux to influence image intensity. As noted above, one technique controls the exposure time of the image. There are other techniques that can be used to control of the intensity of the light transmitted to the sensor. For example, filters, apertures, etc. are used to control the photon flux, which in turn, controls the intensity. Such techniques are well known to the skilled person and not described in detail herein. For purposes of the embodiments of the invention described herein, the light intensity is set constant and exposure time is the variable used to control photon flux integration.

In the embodiments where photon flux is controlled by controlling the exposure time, initial exposure time values are obtained from system calibration. The system is calibrated using a library of calibration plates. Baseline calibration is obtained as a function of plate type and media type. When the system is used to interrogate new growth plates the calibration data for a particular plate type and media type is selected. In this regard, growth plates can be: mono-plates (i.e. for one media); bi-plates (two media); tri-plates (three media), etc. Each type of growth plate present unique imaging challenges. The calibration provides a default exposure time for capturing the first image (image N=1) of the growth plate. The calibration also makes it possible for the system (or system operator) to determine which parts of the image are plate (i.e. not background) and, of the plate portions of the image, which portions are media (the nutrients used to cultivate the colonies) and which portions are, at least potentially, colonies.

Image N=1 of a growth plate is captured using the default values obtained from calibration. If an averaging technique is used to capture the digital images of the growth plate, the bright pixels will have a better signal-to-noise ratio (SNR) than the dark pixels. In the method described herein, signals are isolated for individual pixels, regardless of whether the pixels are light or dark. For a predetermined number of pixels, the intensity, exposure time and SNR are determined. A "map" of these values in the image context is prepared. From this map, a new exposure time that will preferably not saturate more than a predetermined fraction of pixels is selected for the N+1 image acquisition. Preferably, an exposure time in which only a very small fraction of pixels (or less) are saturated is determined and used to capture the final image.

From this a map of the SNR for each pixel where the SNR is updated (i.e. the grey value is refined and the SNR improved for the non-saturated pixels) for each non-saturated pixel is generated. An image is simulated based on this map.

An optimization function algorithm is used to map each grey value intensity for each pixel to the required exposure time corresponding to the optimal SNR for the pixel. The optimization algorithm begins by looking at the initial image (N=1), which was captured using the predetermined default exposure time. An intensity, exposure, and SNR map is generated for the entire image. The exposure time for each pixel is adjusted based on image N and another image (N+1) is captured. As stated above, the new exposure time is chosen that will saturate the signals of the dark parts, resulting in overexposure of the light parts. The intensity map, exposure map, and SNR map are updated for each pixel. This is an iterative process and images are acquired until the maximum SNR for each pixel for the image is reached, or the maximum number of images is reached, or the maximum allotted time has been reached.

Essentially, the dark spots remain dark, the bright spots remain bright and the SNR is improved. The agar growth medium acts as the background for the digital images. A pixel in the image that is different in some way (i.e. a different intensity) from previous images indicates that either the colony is growing or there is contamination (e.g. dust) on the plate. This technique can be used to look at multiple plates at one time.

As the SNR is significantly improved, details can be revealed (with confidence) that could not be seen/trusted allowing for detection of very early small colonies in timed plate imaging. The systems and methods also provide images corresponding to an optimal exposure time that corresponds to specific and controlled saturation over the scene or object of interest.

Once the image acquisition at time $t_0$ is complete, the process of iterative image acquisition is stopped for that time interval. When the predetermined time interval from $t_0$ to $t_1$ has elapsed, the iterative image acquisition process is repeated until the desired confidence in the integrity of the image so acquired has been obtained. The signal to noise ratio is inversely proportional to the standard deviation (i.e. SNR=gv'/standard deviation.) Therefore, an image acquisition that yields a maximum SNR per pixel (i.e. a minimum standard deviation per pixel) will provide an image with a high confidence associated with a time "$T_x$". For example, a high SNR image is obtained for a plate that has been incubated for four hours ($T_1$=4 hours). Another high SNR image of the same plate is obtained after the plate has been incubated for an additional four hours ($T_x$=8 hours).

Once an image associated with a subsequent time ($T_{x+1}$) is obtained, that image (or at least selected pixels of the image associated with an object of interest) can be compared with the image associated with the previous time ($T_x$) to determine if the subsequent image provides evidence of microbial growth and to determine the further processing of the plate.

DETAILED DESCRIPTION

Figure 1:
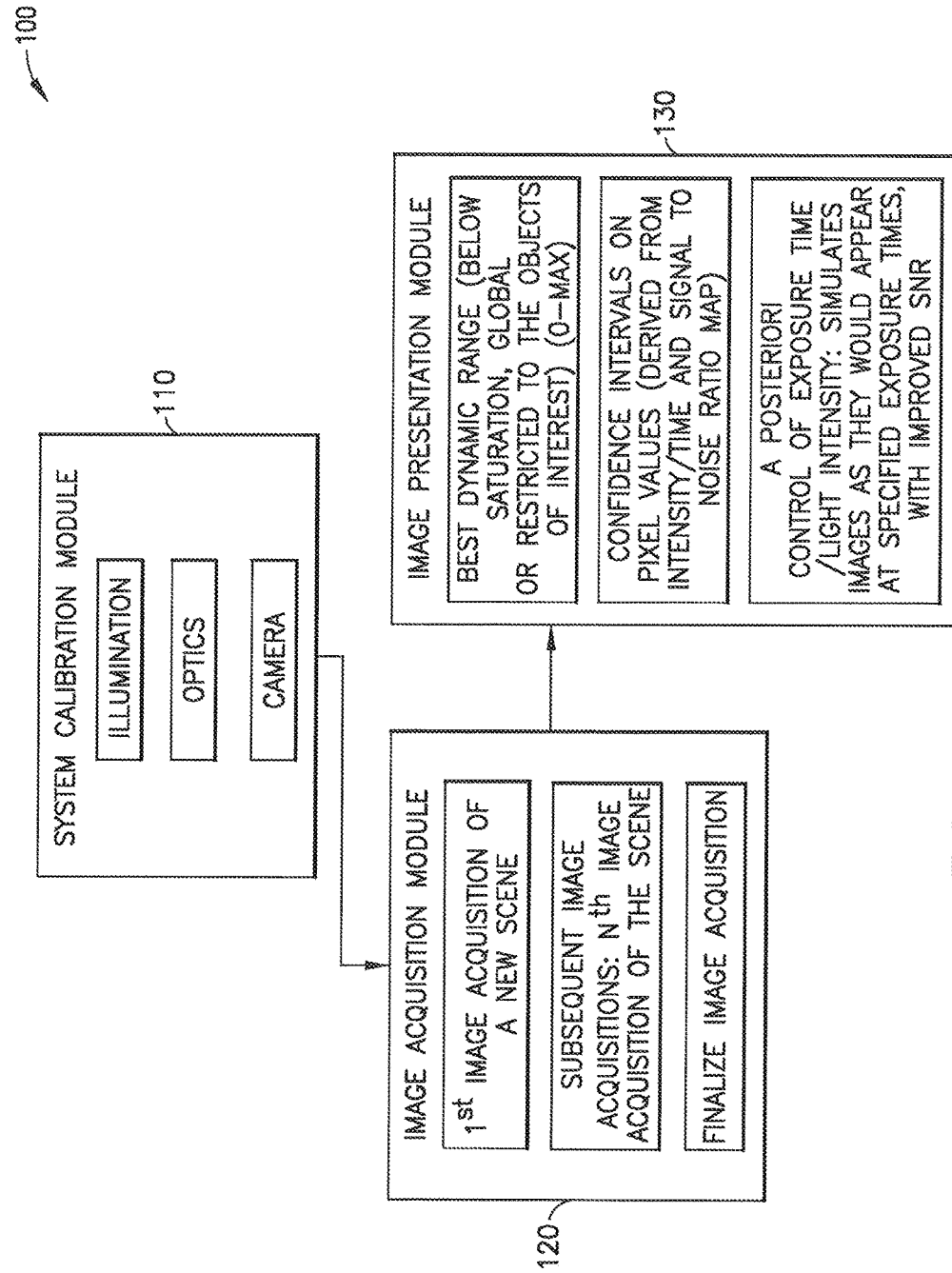
FIG. 1 is a schematic description of a three module system for image acquisition and presentation according to one embodiment of the present invention.

The system described herein is capable of being implemented in optical systems for imaging microbiology samples for the identification of microbes and the detection of microbial growth of such microbes. There are many such commercially available systems, which are not described in detail herein. One example is the BD Kiestra™ ReadA Compact intelligent incubation and imaging system ($2^{nd}$ generation BD Kiestra™ incubator). Such optical imaging platforms have been commercially available for many years (originally CamerA PrimerA from Kiestra® Lab Automation), and are therefore well known to one skilled in the art and not described in detail herein. In one embodiment, the system is a non-transitory computer-readable medium (e.g. a software program) that cooperates with an image acquisition device (e.g. a camera), that provides high quality imaging of an image by interacting to provide a maximum Signal to Noise Ratio (SNR) for every pixel in the image. For each pixel and each color (e.g. channel), the intensity and exposure time are recorded and the system then predicts the next best exposure time to improve on the SNR of the whole scene or objects of interest in the scene. One skilled in the art will appreciate that the multiple values obtained per pixel will depend upon the pixels and the imaging system. For example, in an RBG imaging system, values are obtained for each channel (i.e., red, green, or blue). In other systems, the values are obtained for different spectral bands or wavelengths.

Initially, the system is calibrated. Calibration of imaging systems such as the one described herein are well known to one skilled in the art. A variety of calibration approaches are known. Described herein are examples of system calibration that provide a baseline against which the captured images are evaluated. During calibration, calibration plates (e.g. plates with media but no colonies) are used and the system image acquisition is calibrated against the known input. A library of calibration values for each type of plate media is created, and the calibration data used for a particular plate is selected based on the media in the test plate. Both the system and the data are calibrated. For data calibration, SNR, Linearity, Black level, etc. are determined for each pixel of the captured image of the calibration plate. System calibration includes, but is not limited to, lens distortion, chromatic aberrations, spatial resolution, etc.

Following calibration, images of new plates are acquired. The pixels in the image are analyzed in real time in order to estimate the exposure time that will improve the SNR of the pixels with an SNR that is either below a predetermined threshold or for those pixels with the lowest SNR. Typical imaging systems only retain intensity values for the pixels in the image. In the embodiments described herein, intensity and exposure time are recorded for each pixel. The same pixel is imaged at different exposure times and intensity information is combined to generate high SNR data. From this information, an image can be generated for any specified exposure time, or the best exposure time can be extracted to control pixel saturation.

From a quantitative aspect, due to high SNR, the confidence on subtle intensity variations, on colors and texture is greatly improved allowing a better performance of subsequent object recognition or database comparison. The analysis is done on a grey scale with comparison both to the grey value of the pixel in a prior image (i.e. for image N, the value of the pixel in image N−1). In addition to comparison of the same pixel grey value in the prior image, the pixel grey value of adjacent pixels is also compared with the pixel grey value to determine differences (e.g. the colony/media interface).

SNR of dark of colored objects is uneven in the different channels or very poor when compared to bright objects. In order to improve on this, the system and method described herein deploy an image detection module in which object detection is based upon contrast, SNR, and size/resolution. SNR is improved in both dark and bright regions. Standard deviation is decreased and therefore local contrast is made as significant in bright and dark regions. The goal here is to provide a system that will detect even subtle differences between the x and x+1 time interval images of a plate suspected to contain a growing culture. Those differences must be distinguishable from the "noise" that results from signal variations but not changes in the sample attributable to a growing culture. The systems and methods described herein are especially valuable when objects of interest in the scene may exhibit very different colors and intensities (reflectance or absorbance).

Specifically, the system and method provide automatic adaptation of the dynamic range (extended dynamic range) to accommodate the scene. The system and method provides both the minimum exposure time for saturating the brightest pixel and the maximum exposure time for saturating the darkest pixel (within physical and electronic constraints of the image acquisition equipment (e.g. the camera)). The system and method provide for faster convergence towards a minimum SNR per pixel when compared to image averaging. The system and method provide for improved confidence on colors. Specifically, the SNR for red, green and blue values are homogenized regardless of intensity disparities in red, green, and blue colors.

Intensity confidence intervals are known per pixel, which is very valuable for any subsequent classification effort. The SNR optimization provided by the system and method can be supervised (weighting of detected objects of interest to compute next image acquisition's exposure times).

Intensity, exposure time and estimate SNR are determined from calibration and physics theory for each pixel. To further improve on image quality, chromatic aberration and lens distortion are also calibrated and corrected to render an image free of such defects.

The system and method can control pixel SNR for the image either in an automatic mode or a supervised mode where certain portions of the image are of particular interest. In the automatic mode, the whole image of the scene is optimized, and all pixels are treated equally. In the supervised mode, the scene is further analyzed when acquired to detect the objects of interest. SNR maximization favors the objects of interest regions.

In automatic mode, the image acquisition will stop after the first of the three following conditions occurs: (1) a minimum level of SNR is reached for each and every pixel; (2) a predetermined number of acquisitions have been performed on this scene; or (3) the maximum allowed acquisition time has been reached.

Referring to FIG. 1, a schematic of the system of one embodiment is illustrated. The system 100 has three modules. The first is a system calibration module 110. The calibration module calibrates the illumination of the image, the optics used to collect the image, and the baseline data for the new plate under evaluation by the system.

The image acquisition module 120 is in communication with the system calibration module 110. The image acquisition module captures an image of the object under analysis. The image is captured using exposure time and other criteria determined in a manner described in detail hereinbelow in the context of specific examples. As discussed above, image acquisition proceeds in an iterative manner until a predetermined SNR threshold is met for each pixel or until a predetermined number of images have been captured. The image presentation module 130 provides the image with the best dynamic range (i.e. the brightest non-saturating pixels that are just below saturation), either globally (i.e. in automatic mode) or restricted to the objects of interest (i.e. in supervised mode).

Figure 2:
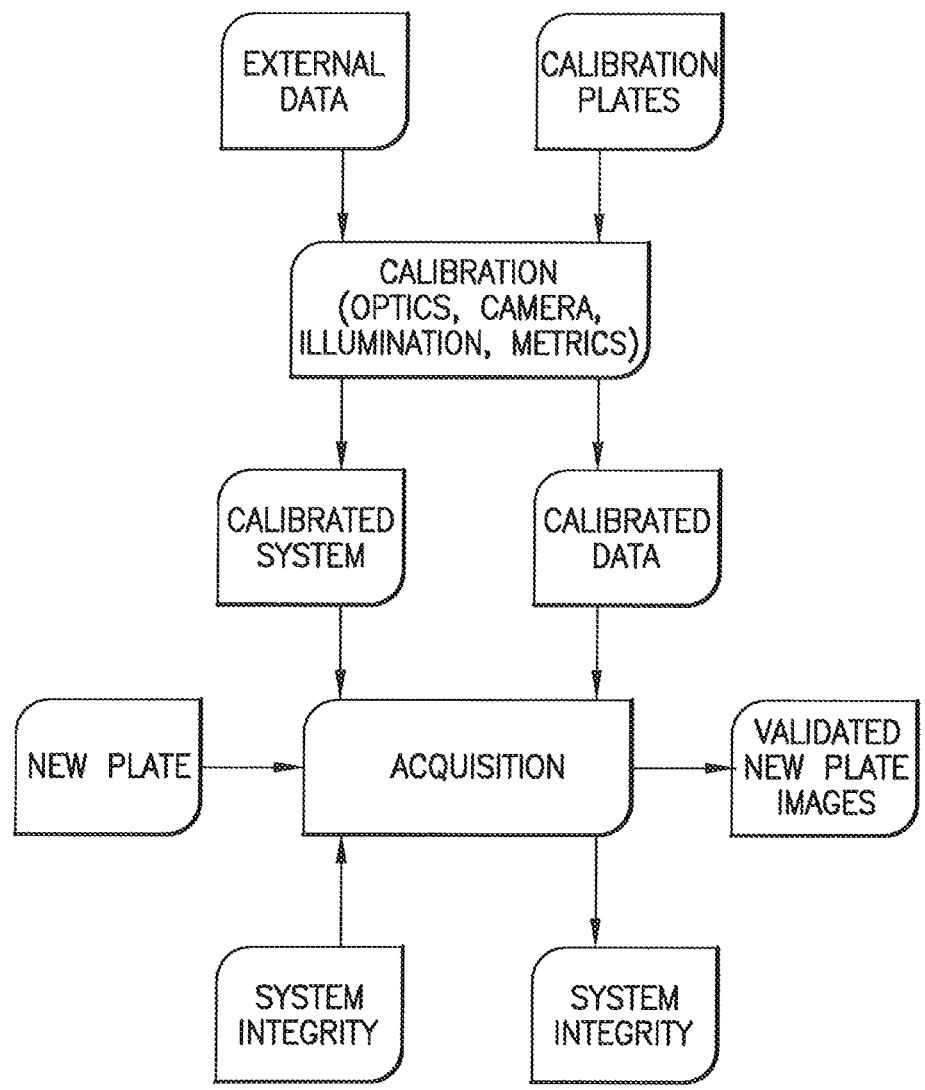
FIG. 2 is a flowchart of system operation for the three module system illustrated in FIG. 1.

Referring to FIG. 2, both external data and calibration plates (i.e. the range of combinations of test plates and culture media) are used to calibrate the system). From the calibration, both system calibration and data calibration are determined. The system and data calibration values are used in image acquisition for a new plate. The calibration is used to validate the new image in terms of the image map (i.e. which pixels are regions outside the plate, which are inside the plate but media with no colonies and which regions reveal colonies).

Figure 3:
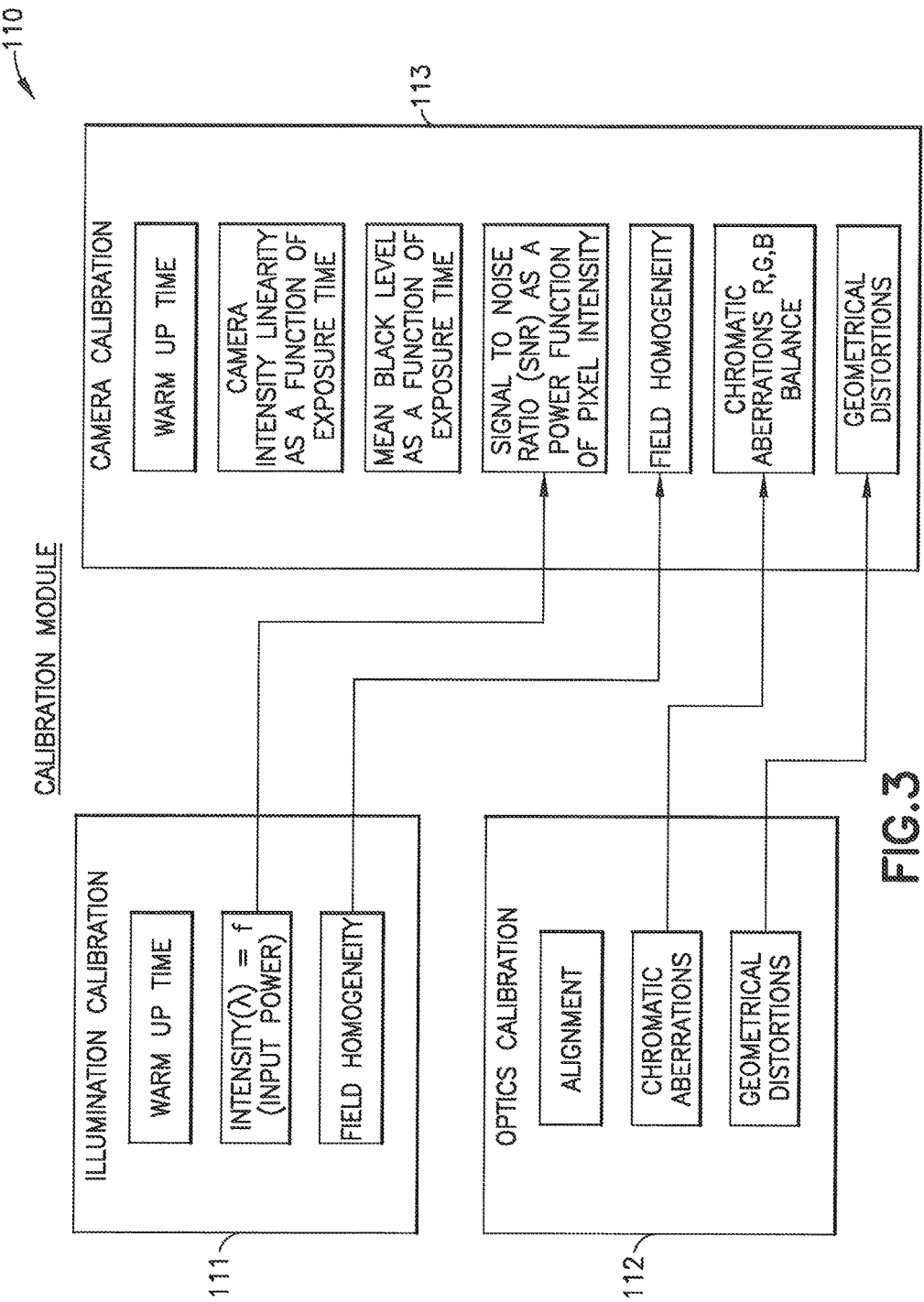
FIG. 3 is a description of the functions of the calibration module illustrated in FIG. 1 for illumination calibration, optics calibration, and camera calibration according to one embodiment of the present invention.

FIG. 3 further illustrates the specific aspects of the system equipment that are calibrated. For the illumination component(s) 111 the warm up time, intensity ($\lambda$)=f (input power) and field homogeneity are determined. Again, for the test plates, the media should be homogeneous for the applicable region (i.e. the entire plate for a mono-plate, half the plate for a bi-plate and a third of a plate for a tri-plate). For the optics calibration 112, alignment, chromatic aberrations and geometrical distortions are determined. For camera calibration 113, baseline levels are determined. Such baseline data are: warm up time; linearity (fixed relationship of grey values and number of photons that reach the sensor) and black level as functions of exposure time, SNR as a function of pixel intensity; field homogeneity; chromatic aberrations; and geometrical distortions are all determined as a baseline against which the acquired image is evaluated. Such baseline data is well known to one skilled in the art and not described in further detail.

Figure 4:
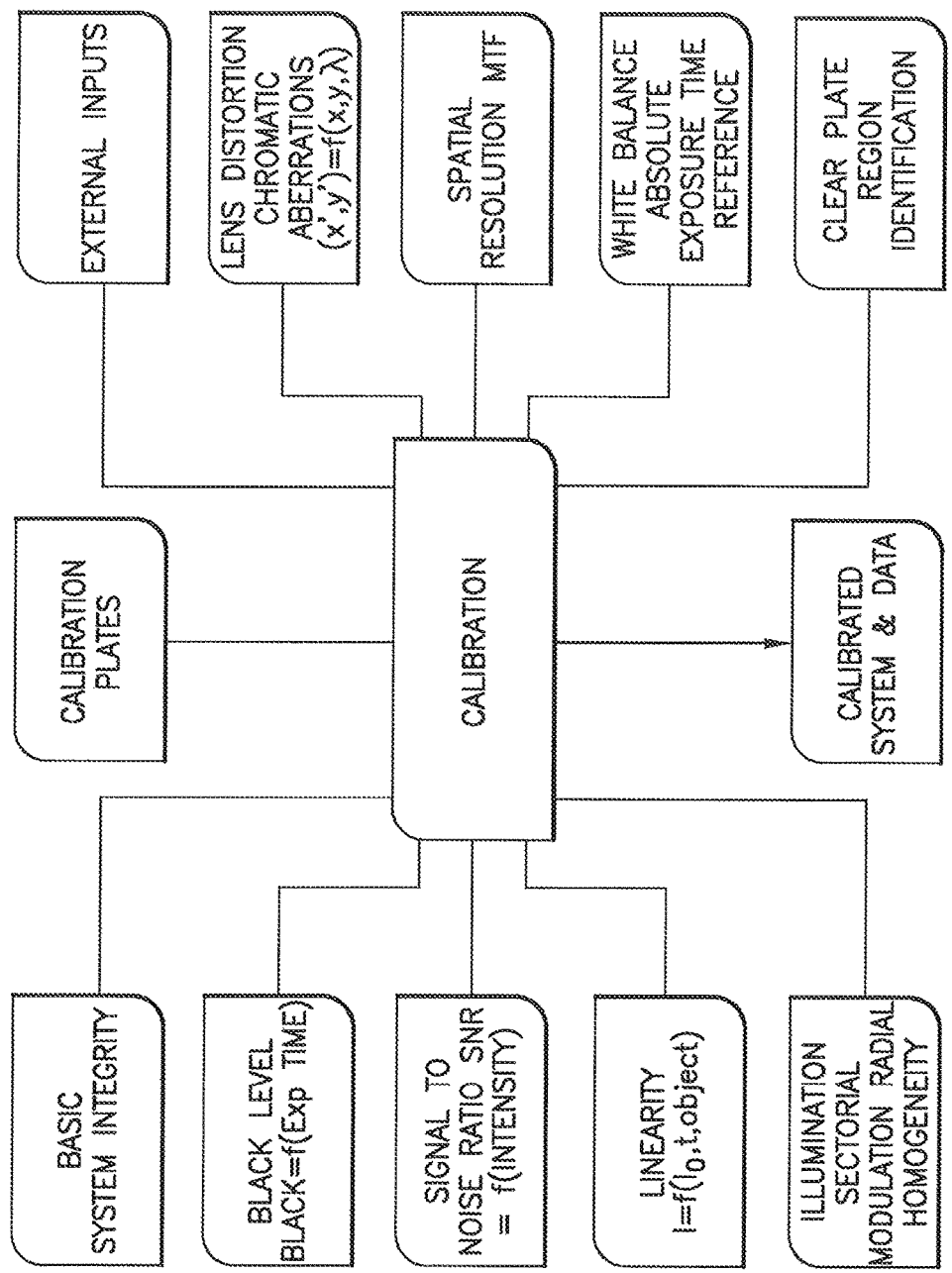
FIG. 4 is an illustration of the data determined from the calibration plates to calibrate the system of FIG. 1 according to one embodiment.

FIG. 4 is further detail on the inputs into the calibration system (i.e. system information, the library of calibration plates and other inputs). For each calibration plate, an image is obtained and each pixel is assigned values for black level, SNR, linearity and illumination. For the system (i.e. not pixel by pixel) model values that reflect system factors such as distortion, chromatic aberrations, spatial resolution and white balance are determined. These values are all collected to provide a calibrated system and calibrated data for use in the evaluation of plates. As noted below, these values are used to finalize image acquisition.

Figure 5:
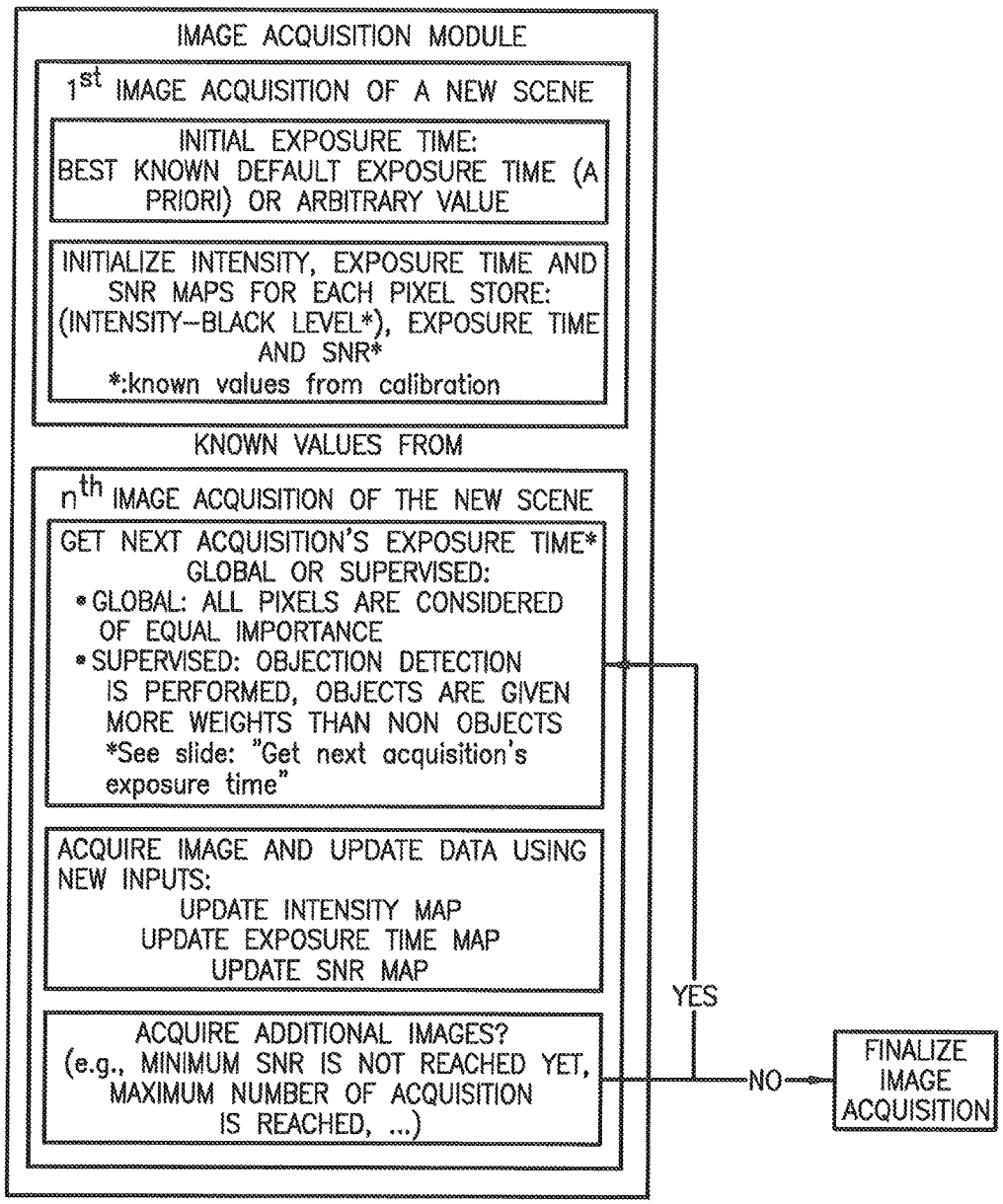
FIG. 5 is a description of the functions of the image acquisition module illustrated in FIG. 1 according to one embodiment of the present invention.

More details about the image acquisition module are described in FIG. 5. In the first step, an image is acquired using default values. From this first image, the intensity, exposure time, and SNR for each pixel are determined. The intensity is determined by subtracting the "black level" for the pixel from a measured intensity value. The black level and SNR are obtained from the calibration previously described.

Image acquisition occurs at times $t_0, t_1, \ldots t_x$. At each time, an image is acquired through a series of N image acquisitions. The series of N image acquisitions iterates to a SNR for the acquired image that correlates with high confidence in image integrity.

Figure 6:
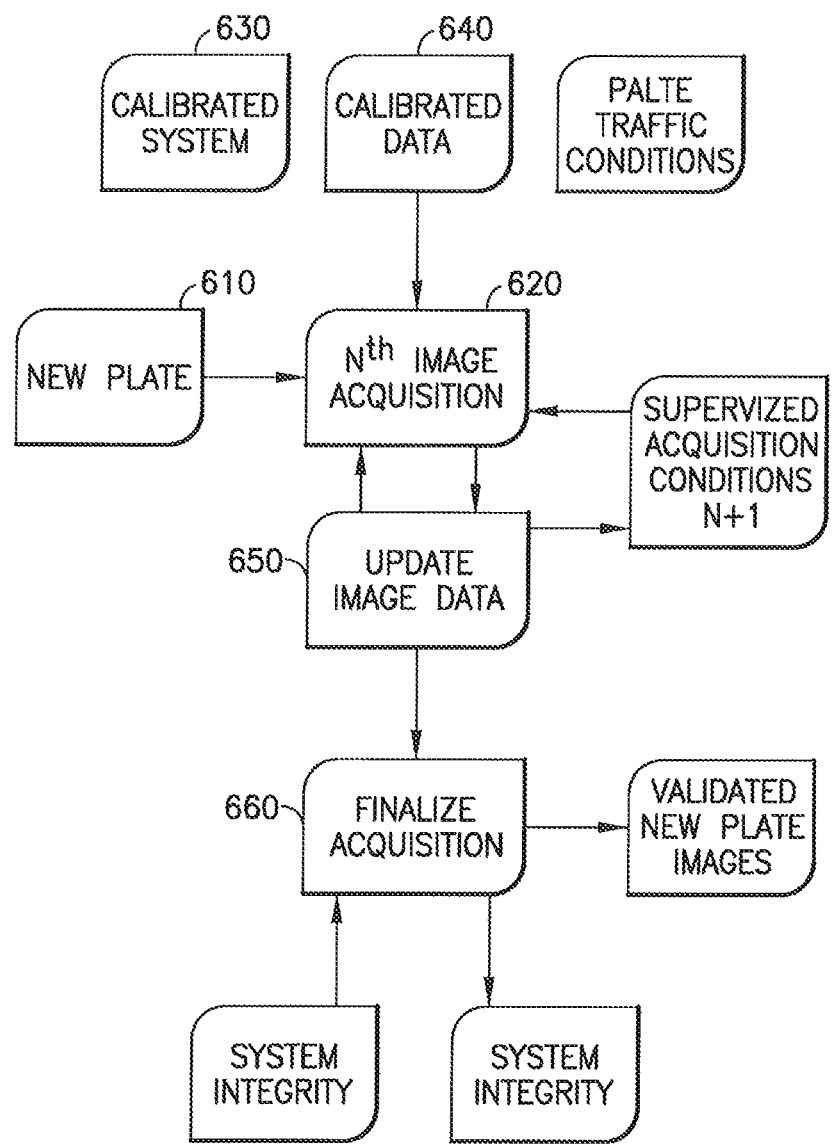
FIG. 6 is a schematic of the method of image acquisition using the system of FIG. 1 according to one embodiment.

Image acquisition at a given time (e.g. $t_0$) and update is illustrated in FIG. 6. The image of a new plate 610 is acquired in step 620. Image acquisition is informed by the system 630 and data 640 calibration. Plate traffic conditions (i.e. number of plates per unit time) are also used to calibrate and control the system. At a later point in time during the image acquisition process, a subsequent image is acquired 650 and compared with the prior image (either automatically or supervised). Typically, there will be about four to about ten image acquisitions at each time interval to obtain an image with an acceptable confidence. Once the desired SNR for the selected object is obtained, the exposure time is determined for the final image acquisition 660.

According to one embodiment, the pixels are updated as follows. Grey value, reference exposure time and signal to noise ratio represent the information stored for each illumination configuration (top, side, bottom, or a mixture of them) per plate (image object). This information is updated after each new acquisition. To start with, this information is updated using the first image acquisition (N=1).

Grey value, reference exposure time and signal to noise ratio represent the information stored for each illumination configuration (top, side, bottom, or a mixture of them) per plate. This information is updated after each new acquisition. To start with this information is initialized according to the first image acquisition (N=1). In one embodiment, $gv_{x,y,1}$ is a grey value (gv) at image position (x,y) corresponding to the $1^{st}$ image capture (N=1) of the plate using exposure time $E_1$ and respective Signal to Noise Ratio ($SNR_{gv}$). In this embodiment:

$black_{x,y,E_1}$ is the black reference value point in (x,y) corresponding to exposure time $E_1$;

$E'_{x,y,1}$ is the updated reference time point in (x,y) after 1 acquisition;

$gv'_{x,y,1,E_1}$ is the updated grey value in x,y after 1 acquisition at $E'_{x,y,1}$ equivalent exposure time;

$SNR'_{x,y,1}$ is the updated SNR in x, y after 1 acquisition;

$$E'_{x,y,1} = E_1$$

$$gv'_{x,y,1,E'_{x,y,1}} = gv_{x,y,1} - black_{x,y,E_1}$$

$$SNR'_{x,y,N} = \begin{cases} SNR_{gv_{x,y,1}} \\ 0 \text{ if } gv_{x,y,1} \text{ is saturating} \end{cases}$$

The black level is noisy and the iterative image acquisition process obtains an image that is "less noisy" (i.e. an image with a higher confidence level). The black value is a default value that is not recalculated during image acquisition. The black value is a function of exposure time.

SNR=0 when a pixel is saturating for a given exposure time (hence no improvement in SNR) and light source intensity. Only values from the non-saturated pixels are updated.

N=1: The initial exposure time is the best known default exposure time (a priori), or an arbitrary value $$\left(\text{e.g.:} \frac{\text{Max exposure time} + \text{Min Exposure time}}{2}\right).$$

This is determined from calibration for the particular plate and media for the new plate under analysis.

Grey value, reference exposure time and signal to noise ratio are updated after each new image acquisition (i.e. N=2, 3, 4 . . . N) according to the following embodiment. Grey value $gv_{x,y,N}$ for image position (x,y) corresponds to the Nth image capture of the plate using exposure time $E_N$ and respective Signal to Noise Ratio ($SNR_{x,y,N}$). In this embodiment:

$black_{x,y,E_N}$ is the black reference value point in (x,y) corresponding to exposure time $E_N$;

$E'_{x,y,N}$ is the updated reference time point in (x,y) after N acquisitions;

$gv'_{x,y,N,E_N}$ is the updated grey value in (x,y) after N acquisitions at $E'_{x,y,N}$ equivalent exposure time; and $SNR'_{x,y,N}$ is the updated SNR in x,y after N acquisitions.

$$E'_{x,y,N} = \begin{cases} \text{MIN}(E'_{x,y,N-1}, E_N) & \text{if } gv'_{x,y,N-1,E_{x,y,N-1}} \text{ or } gv_{x,y,N} \text{ are saturating} \\ \text{MAX}(E'_{x,y,N-1}, E_N) & \text{else} \end{cases}$$

$$gv'_{x,y,N,E'_{x,y,N}} = E'_{x,y,N} \times \frac{\frac{gv'_{x,y,N-1,E'_{x,y,N-1}}}{E'_{x,y,N-1}} \times SNR'^2_{x,y,N-1} + \frac{gv_{x,y,N} - black_{x,y,E_N}}{E_N} \times SNR^2_{x,y,N}}{SNR'^2_{x,y,N-1} + SNR^2_{x,y,N}}$$

$$SNR'_{x,y,N} = \sqrt{SNR'^2_{x,y,N-1} + SNR^2_{x,y,N}}$$

Therefore, the updated SNR for a pixel in the Nth image acquisition is the square root of the squared updated signal to noise ratio of the prior image acquisition and the squared signal to noise ratio of the current image acquisition. Each acquisition provides an updated value (e.g. $E'_{x,y,N}$) for each pixel. That updated value is then used to calculate the updated value for the next image acquisition. SNR=0 for a pixel when a pixel is saturating for a given exposure time and light source intensity. Only the non-saturated pixels are updated. The $N^{th}$ exposure time corresponds to a supervised optimization the goal of which is to maximize the SNR for the objects of interest. The object of interest can be the entire plate, the colonies, a portion of the plate, or the whole image.

After updating the image data with a new acquisition, the acquisition system is able to propose the best next acquisition time that would maximize SNR according to environmental constraints (minimum required SNR, saturation constraints, maximum allowed acquisition time, region of interest). In embodiments where image acquisition is supervised: x,y $\in$ object implies that in supervised mode, object pixels only are considered for the evaluations. In those embodiments where image acquisition is not supervised, the default object is the entire image.

Figure 7:
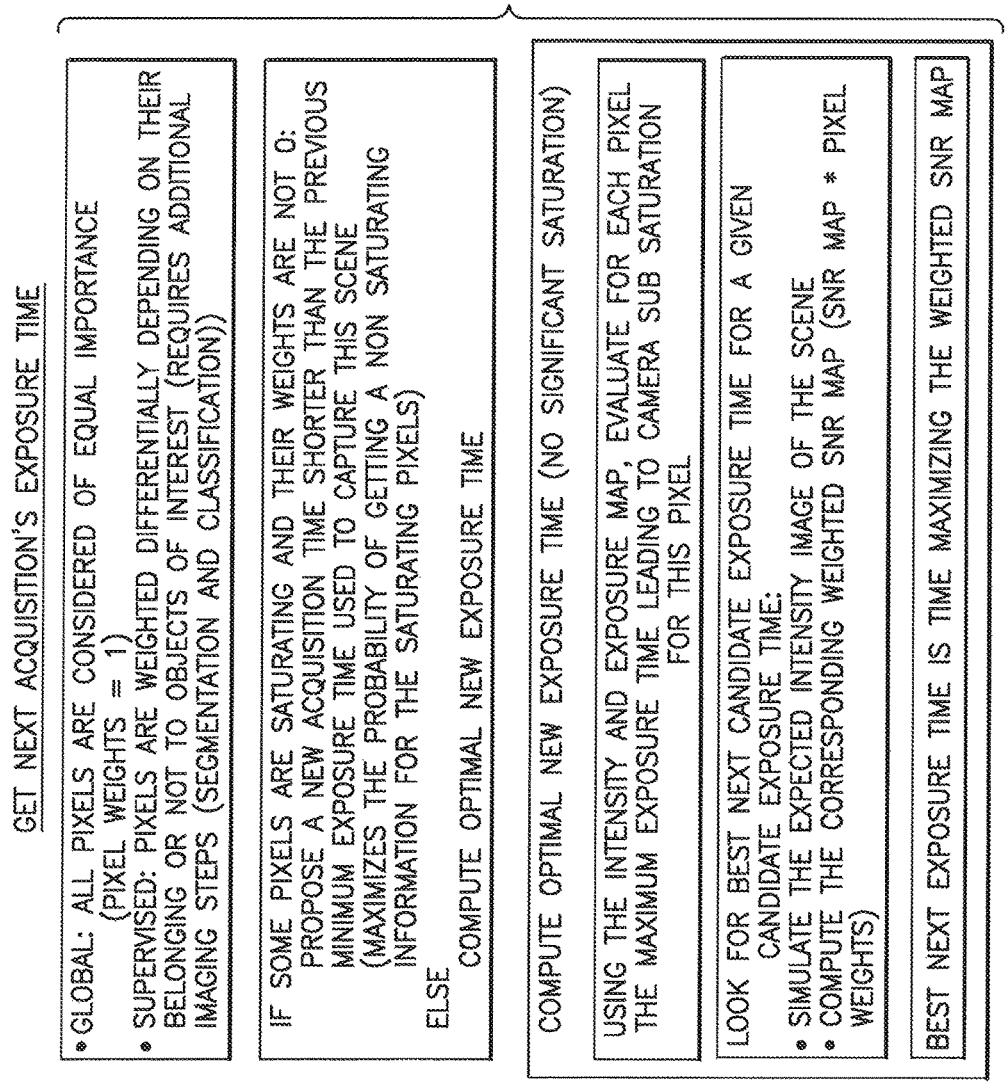
FIG. 7 is more detailed description of the functions performed by the image acquisition module illustrated in FIG. 5.

With reference to FIG. 7, from the acquired image analysis, the exposure time for the next image (N+1) in the image acquisition series at a given time interval is determined using either the automatic mode or supervised mode described above. Referring to FIG. 7, for the automated process, each pixel is weighted equally (i.e. assigned a value of 1). For the supervised approach, pixels associated with objects (e.g. cultures) are weighted differently. The supervised process requires additional imaging steps. If a significant fraction (e.g. greater than 1 in 100,000) of pixels are saturating and their weights are not 0, then a new exposure time is proposed that is shorter (e.g. ⅕th) than the previous minimum exposure time used to capture the image. This adjustment improves the probability of getting non-saturated information for the saturating pixels. In alternative embodiments a new exposure time is calculated. If there is no significant pixel saturation, then, for each pixel, from the exposure and intensity map, the maximum exposure time that will not result in pixel saturation is determined. From this an exposure time for the image is determined, and an intensity image is simulated. From this, the corresponding weighted SNR map is determined.

Figure 8:
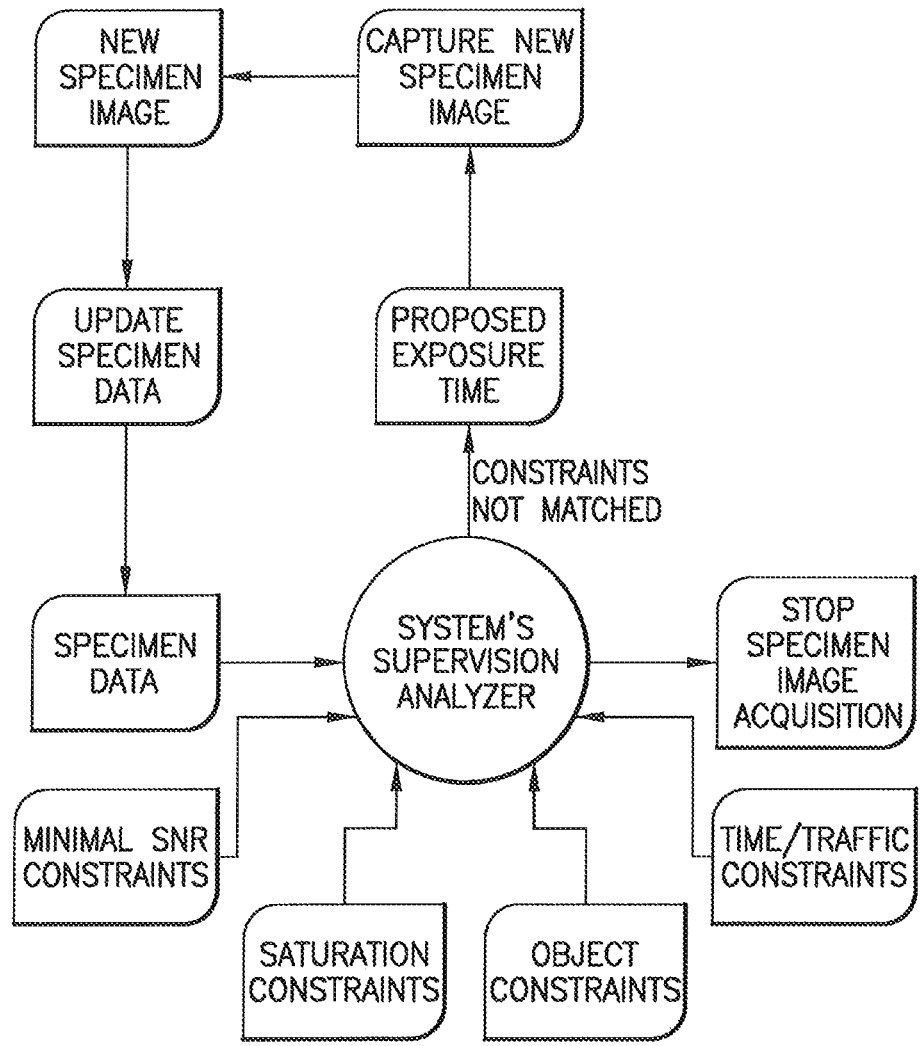
FIG. 8 illustrates the method for choosing the next image acquisition time according to one embodiment.

Referring to FIG. 8, the specimen image is used to update the image data, pixel by pixel, in the image map. That specimen data is then fed to the image analyzer and image analysis is performed informed by predetermined constraints on the SNR for each pixel, other saturation constraints, object constraints, etc. and time or traffic constraints (i.e. the duration of the capture and analysis).

In one embodiment specifically, the acquired image is analyzed pixel by pixel for saturated pixels. If $E_N$ results in pixel saturation that exceeds predetermined limits, a lower value for $E_{N+1}$ is selected. For example, if the minimal exposure time was not acquired yet and the % of saturated pixels $$\left(gv'_{x,y,N,E'_{x,y,N}} = gv_{sat}\right)$$

exceeds the predetermined limit (e.g. >1/10$^5$) a new exposure time is proposed at a predetermined increment (e.g. a fifth of the minimal exposure time previously used). The lower limit (i.e. the minimum acceptable exposure time) is also predetermined. These constraints on exposure time permit faster convergence towards non-saturating image acquisition conditions.

A new image is acquired at the new exposure time. For the new image, secondary checked constraints are the minimum desired SNR per pixel (this is the lower SNR threshold) and overall acquisition time (or $N_{max}$) allowed for this image. If the overall acquisition time for this scene has reached the time limit or if every updated SNR for each pixel is such that $SNR'_{x,y,N} \geq MinSNR$, then the image data is considered acceptable and the acquisition of the scene ends for the time interval (e.g. $t_0$). When image acquisition commences at time $t_x$ (e.g. time $t_1$) the best exposure time ($E_{Nfinal}$) leading to sub-saturation conditions from the previous acquisition (e.g. at time $t_0$) exposure is used as the initial value for E. The process for image acquisition at $t_x$ is otherwise identical to the process at time $t_0$.

If the saturation constraint is lifted (no significant saturation) the next optimal exposure time is determined and investigated. First, the exposure time boundary limits are computed over the region of interest. These exposure time boundaries are: i) the exposure time to saturate the brightest pixels; and ii) the exposure time to saturate the darkest pixels.

The exposure time for saturating the brightest non-saturated pixels, $E_{min}$, is determined from the grey value $gv_{max}$ that corresponds to the absolute maximum intensity and $E'_{gv_{max}}$ (its related exposure time) from the following:

$$gv_{max} = gv'_{x,y,N,E'_{x,y,N}} \text{ with } \begin{cases} \dfrac{gv'_{x,y,N,E'_{x,y,N}}}{E'_{x,y,N}} \text{ is Maximum} \\ gv'_{x,y,N,E'_{x,y,N}} \neq gv_{sat} \end{cases},$$

$$E'_{gv_{max}} = gv_{max} \text{ related } E'_{x,y,N}$$

$$E_{min} = E'_{gv_{max}} \times \frac{gv_{sat}}{\max(gv_{max}, 1)}$$

The exposure time for saturating the darkest pixels, $E_{max}$, is determined from the grey value $gv_{min}$ that corresponds to the absolute minimum intensity and $E'_{gv_{min}}$ is its related exposure time:

$$gv_{min} = gv'_{x,y,N,E'_{x,y,N}} \text{ with } \begin{cases} \dfrac{gv'_{x,y,N,E'_{x,y,N}}}{E'_{x,y,N}} \text{ is Minimum} \\ gv'_{x,y,N,E'_{x,y,N}} \neq gv_{sat} \end{cases},$$

$$E'_{gv_{min}} = gv_{min} \text{ related } E'_{x,y,N}$$

$$E_{max} = E'_{gv_{min}} \times \frac{gv_{sat}}{\max(gv_{min}, 1)}$$

The next optimal exposure time is chosen among all candidate exposure times within $E_{max}$ and $E_{min}$ by simulation. Specifically, an exposure time is determined by simulation that will maximize the updated mean SNR (for all pixels below the minimum signal to noise ratio threshold), after adding the simulated image at tested exposure time $E_{test,N+1}$. The simulated image at $E_{test,N+1}$ is generated as follows (for each and every pixel).

Grey value $$gv'_{x,y,N,E'_{x,y,N}}$$

is pixel data corresponding to the current updated image data. If a new time point $E_{test,N+1}$ is selected, the expected grey value is:

$$gv_{x,y,E_{test,N+1}} = \min\left(gv'_{x,y,N,E'_{x,y,N}} \times \frac{E_{test,N+1}}{E'_{x,y,N}} + \text{black}_{x,y,E_{test,N+1}}, gv_{sat}\right)$$

After updating this value with a value for the pixel from the simulated image at time point $E_{test,N+1}$ image, the SNR for this (x,y) pixel will be:

$$SNR'_{x,y,N+1} = \sqrt{SNR'_{x,y,N}{}^2 + SNR_{x,y,N+1}{}^2}$$

The next best exposure time $E_{best,N+1}$ is then determined by:

$$E_{best,N+1} = E_{test,N+1} \in [E_{min}, E_{max}];$$

with $\Sigma_{x,y, \in object}{}^{E_{test,N+1}} SNR'_{x,y,N+1}$ being maximum.

If image acquisition and analysis is supervised x,y ∈ object the SNR is integrated for the objects of interest only. In automatic mode the object is the whole image.

Figure 9:
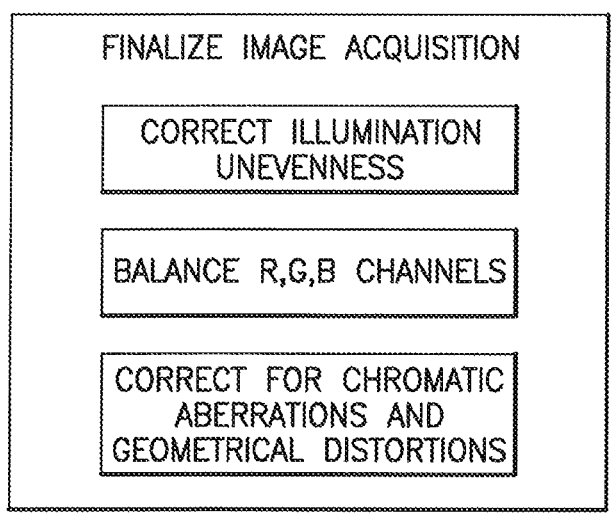
FIG. 9 is a description of the steps taken to finalize image acquisition.

FIG. 9 describes the final steps for image acquisition. Those steps are conventional image processing techniques well known to one skilled in the art and not described in detail herein.

Figure 10:
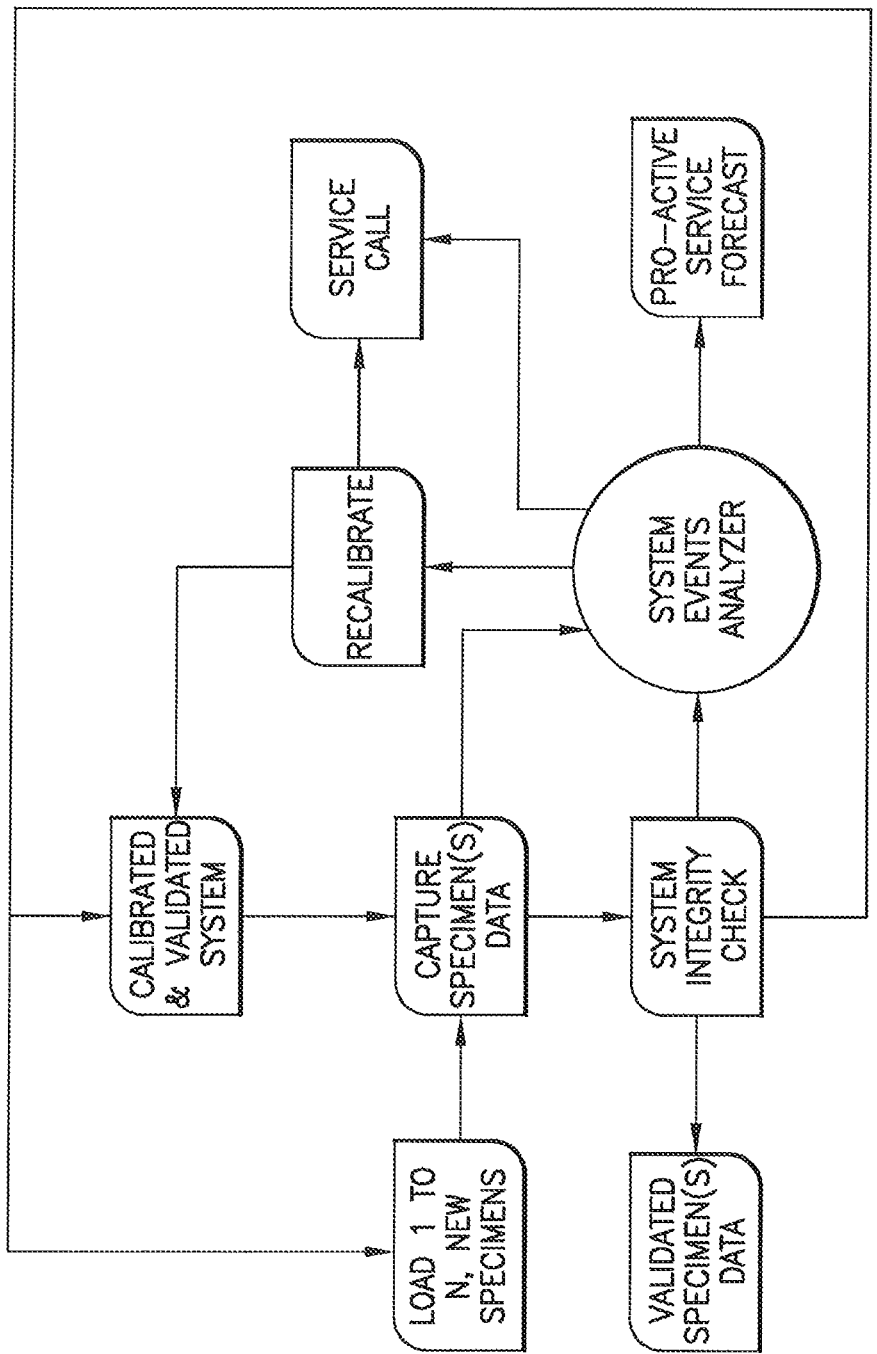
FIG. 10 is a process flow schematic of how to determine system integrity.

FIG. 10 illustrates the method by which system integrity is determined during image acquisition. Note that, once system integrity is checked, specimens are loaded into the system and the data from the specimens is captured. The data capture is informed by the calibration information as discussed above. The captured data is provided to both the system integrity check and a system events analyzer.

Once the image has been obtained as described above it is compared with an image of the plate that has been incubated for a different amount of time. For example, an image of a plate is obtained as described herein after the plate has been incubated for four hours ($T_1=4$). After four or more hours, another image of the plate is obtained as described above ($T_x=8$ hrs). The high SNR image obtained at $T_{x+1}$ can then be compared with the high SNR image at $T_x$. Changes in the two images are evaluated to ascertain evidence of microbial growth. Decisions on further processing (e.g. plate is positive, plate is negative, plate requires further incubation) are based on this comparison.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for imaging biological samples disposed in culture media, the system comprising:
   a system calibration module that provides default values for capturing an image of a biological sample disposed on culture media disposed in a plate;
   an image acquisition module comprising a camera wherein the image acquisition module is adapted to acquire data for a series of images at a given time interval, in communication with the system calibration module, the image acquisition configured to: i) acquire data for a first image using default values for photon flux and exposure time from the system calibration module and creating a pixel by pixel map of the image data, each pixel associated with a signal to noise ratio, a photon flux and exposure time, and an intensity; ii) update the image acquisition by reviewing the image data to identify saturated pixels and selecting one of a new photon flux, a new exposure time or both based on whether a ratio of saturated to non-saturated pixels is greater than or less than a predetermined saturation threshold and, based on that determination; iii) use a new value for the photon flux, the exposure time or both to acquire data for a new image and iv) update the map of the image data with the new values for signal to noise ratio, the photon flux, the exposure time or both and pixel intensity,
   wherein the image acquisition module is configured to acquire data for a new image if the signal to noise ratio of unsaturated pixels is less than a predetermined SNR threshold or a number of saturated pixels exceeds the predetermined saturation threshold,
   wherein the image acquisition module finalizes image acquisition when either the signal to noise ratio of unsaturated pixels meets or exceeds the predetermined SNR threshold, a predetermined allocated time for image acquisition has elapsed or a predetermined maximum number of images has been acquired; and
   an image presentation module that transforms the image data from the image acquisition module into an image for viewing or analysis.

2. The system of claim 1 wherein the photon flux is a set value and the system controls a camera sensor integration by controlling exposure time wherein the calibration module determines default photon flux and exposure time for a variety of plates and culture media.

3. The system of claim 2 wherein the new value for the photon flux is obtained by using either a new exposure time or a new light intensity value or both.

4. The system of claim 1 wherein signal to noise ratio is determined for at least a portion of the image of the sample disposed on the culture media.

5. The system of claim 1 wherein the image acquisition module acquires image data from the camera for at least one or more channels or one or more spectral bands.

6. The system of claim 1 wherein the image acquisition module assigns a grey value for each pixel for each image acquisition, and the grey value for each pixel is updated after each image acquisition.

7. The system of claim 6 wherein the updated grey value is the previous grey value minus a predetermined reference value, wherein the predetermined reference value is a predetermined value based on the plate, the plate media and the exposure time for the image acquisition module assigns a grey value for each pixel for each acquisition, and the grey value for each pixel is updated after each image acquisition.

8. The system of claim 1 wherein the image acquisition module is configured to operate in at least one of an automatic mode where all pixels are treated equally or in a supervised mode, where the analyzed pixels are those having been identified as associated with one or more objects of interest.

9. The system of claim 1 wherein the photon flux is a set value and the system controls a camera sensor integration by controlling exposure time.

10. A method for imaging biological samples disposed in culture media, the method comprising:
    determining default values for obtaining an image of a biological sample disposed on culture media supported in a plate;
    acquiring image data corresponding to a series of images at a first time over a first time interval, the data of the first image in the series being acquired using predetermined defaults for photon flux and exposure time;
    creating a pixel by pixel map of the image data;
    associating data for each pixel with a signal to noise ratio, a value for photon flux, exposure time, and an intensity;
    updating at least one of the image photon flux value and exposure time value by:
    i) reviewing the image data for saturated pixels and the signal to noise ratio for the pixels and selecting a new value for at least one of photon flux and exposure time based on whether a ratio of saturated to non-saturated pixels is greater than or less than a predetermined threshold and whether the signal to noise ratio of unsaturated pixels meets or exceeds a predetermined SNR threshold, and based on that determination, using the new value for photon flux, exposure time, or both to acquire a new image and updating the map of the image with the new values for signal to noise ratio, photon flux and exposure time, and pixel intensity;

ii) acquiring data for the new image using the at least one new value for photon flux and exposure time;

iii) optionally repeating steps i) and ii);

finalizing image data acquisition for the time interval when either the image data is at or above the predetermined SNR threshold, a predetermined maximum allotted time for image acquisition has elapsed or a predetermined maximum number of images has been acquired; and repeating the steps of acquiring, creating, associating, updating and finalizing for a second time over a second time interval; and transforming the image data acquired at first and second time intervals into first and second images the first image acquired at the first time and the second image acquired at a second time.

11. The method of claim 10 wherein the value for photon flux is constant and the exposure time value updated and wherein the predetermined default values are based on plate, plate culture and exposure time.

12. The method of claim 10 further comprising determining the pixels for which the image map will be created, wherein the pixels are associated with an object of interest.

13. The method of claim 12 wherein the default values comprise a black level for the pixels associated with an object of interest at a default exposure time.

14. The method of claim 10 wherein the pixel by pixel map is a grey value, the signal to noise ratio and the exposure time for each pixel.

* * * * *